United States Patent
Lei et al.

(10) Patent No.: US 9,318,870 B2
(45) Date of Patent: Apr. 19, 2016

(54) DEEP ULTRA-VIOLET LIGHT SOURCES FOR WAFER AND RETICLE INSPECTION SYSTEMS

(75) Inventors: Gang Lei, Elk Grove, CA (US); Damon F. Kvamme, Los Gatos, CA (US)

(73) Assignee: KLA-Tencor Corporation, Milpitas, CA (US)

(*) Notice: Subject to any disclaimer, the term of this patent is extended or adjusted under 35 U.S.C. 154(b) by 0 days.

(21) Appl. No.: 14/114,737

(22) PCT Filed: May 2, 2012

(86) PCT No.: PCT/US2012/036124
§ 371 (c)(1),
(2), (4) Date: Jan. 9, 2014

(87) PCT Pub. No.: WO2012/154468
PCT Pub. Date: Nov. 15, 2012

(65) Prior Publication Data
US 2014/0111799 A1    Apr. 24, 2014

Related U.S. Application Data (60) Provisional application No. 61/483,540, filed on May 6, 2011.

(51) Int. Cl.
*H01S 3/109* (2006.01)
*H01S 3/23* (2006.01)
(Continued)

(52) U.S. Cl.
CPC ............ *H01S 3/109* (2013.01); *G01N 21/9501* (2013.01); *G02F 1/353* (2013.01);
(Continued)

(58) Field of Classification Search
CPC ...... H01S 3/0092; H01S 3/109; H01S 3/2391; H01S 3/06754; H01S 3/1616; H01S 3/1618; H01S 3/1611
USPC .......................................................... 372/22
See application file for complete search history.

(56) References Cited

U.S. PATENT DOCUMENTS 6,498,801 B1   12/2002   Dudelzak et al.
7,873,204 B2   1/2011    Wihl et al.
(Continued)

FOREIGN PATENT DOCUMENTS

WO    03083450 A1     10/2003
WO    2012154468 A3   11/2012

OTHER PUBLICATIONS

"International Application Serial No. PCT/US2012/036124, Search Report and Written Opinion mailed Oct. 29, 2012", 10 pgs.
(Continued)

*Primary Examiner* — Xinning Niu
(74) *Attorney, Agent, or Firm* — Kwan & Olynick LLP (57) ABSTRACT

Disclosed are methods and apparatus for generating a sub-208 nm laser. A laser apparatus includes one or more seed radiation sources for generating a first radiation beam having a first fundamental wavelength on a first optical path and a second radiation beam having a second fundamental wavelength on a second optical path, a first amplifier for amplifying the first radiation beam, a second amplifier for amplifying the second radiation beam, and a wavelength conversion module comprising a plurality of crystals for frequency multiplying and mixing the amplified first and second radiation beams to produce an output beam at a fifth harmonic that is less than about 208 nm.

10 Claims, 7 Drawing Sheets

(51) Int. Cl.
*H01S 3/00* (2006.01)
*G02F 1/35* (2006.01)
*G01N 21/95* (2006.01)
*H01S 3/067* (2006.01)
*H01S 3/16* (2006.01)

(52) U.S. Cl.
CPC ............ *H01S 3/0092* (2013.01); *H01S 3/2391* (2013.01); *G02F 2001/354* (2013.01); *G02F 2001/3507* (2013.01); *H01S 3/06754* (2013.01); *H01S 3/1611* (2013.01); *H01S 3/1616* (2013.01); *H01S 3/1618* (2013.01)

(56) References Cited

U.S. PATENT DOCUMENTS

| | | | |
|---|---|---|---|
| 8,090,189 | B1 | 1/2012 | Phalke et al. |
| 2005/0002020 | A1* | 1/2005 | Inoue et al. ................. 356/237.1 |
| 2005/0041702 | A1* | 2/2005 | Fermann et al. ................. 372/25 |
| 2006/0222372 | A1* | 10/2006 | Spinelli et al. ................. 398/183 |
| 2007/0263679 | A1* | 11/2007 | Staroudoumov et al. ....... 372/22 |
| 2010/0251203 | A1 | 9/2010 | Abrams et al. |

OTHER PUBLICATIONS

"Int'l Application Serial No. PCT/US2012/036124, Preliminary Report on Patentability mailed Nov. 21, 2013", 7 pgs.

* cited by examiner

DEEP ULTRA-VIOLET LIGHT SOURCES FOR WAFER AND RETICLE INSPECTION SYSTEMS

CROSS-REFERENCE TO RELATED APPLICATION

This application is a U.S. national application under 5 U.S.C. 371 of PCT Application Number PCT/US12/36124, entitled DEEP ULTRA-VIOLET LIGHT SOURCES FOR WAFER AND RETICLE INSPECTION SYSTEMS, filed 2 May 2012 by Gang Lei et al., which claims priority of U.S. Provisional Patent Application No. 61/483,540, entitled DUV 193 nm LIGHT SOURCES FOR APPLICATIONS OF WAFER AND RETICLE INSPECTIONS, filed 6 May 2011 by Gang Lei et al. These applications are herein incorporated by reference in their entirety for all purposes.

TECHNICAL FIELD OF THE INVENTION

The invention generally relates to a field of wafer and reticle inspection. More particularly the present invention relates to apparatus and techniques for providing light sources having a wavelength below 200 nm.

BACKGROUND

Generally, the industry of semiconductor manufacturing involves highly complex techniques for fabricating integrating circuits using semiconductor materials which are layered and patterned onto a substrate, such as silicon. An integrated circuit is typically fabricated from a plurality of reticles. Generation of reticles and subsequent optical inspection of such reticles have become standard steps in the production of semiconductors. Initially, circuit designers provide circuit pattern data, which describes a particular integrated circuit (IC) design, to a reticle production system, or reticle writer.

Due to the large scale of circuit integration and the decreasing size of semiconductor devices, the reticles and fabricated devices have become increasingly sensitive to defects. That is, defects which cause faults in the device are becoming increasingly smaller. The device can generally be required to be fault free prior to shipment to the end users or customers.

Various inspection systems are used within the semiconductor industry to detect defects on a semiconductor reticle or wafer. One type of inspection tool is an optical inspection system. In optical inspection systems, one or more radiation beams are directed towards the semiconductor wafer or reticle and a reflected and/or scattered beam is then detected. The detected beam is used to then generate a detected electrical signal or an image, and such signal or image is then analyzed to determine whether defects are present on the wafer.

Lasers are also used as light sources in many inspection systems to measure defects on reticles or wafers. Lasers provide light with high brightness and can provide a collimated beam of light that can be directed easily through lenses and toward the sample. Additionally, laser sources with a short wavelength, e.g., below 200 nm, may be advantageously used for examining relatively small feature sizes.

There is a continuing need for improved inspection techniques and apparatus having sub-200 nm light sources.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a laser apparatus for generating output radiation having a wavelength below about 208 nm is disclosed. The apparatus includes one or more seed radiation sources for generating a first radiation beam having a first fundamental wavelength on a first optical path and a second radiation beam having a second fundamental wavelength on a second optical path, a first amplifier for amplifying the first radiation beam, a second amplifier for amplifying the second radiation beam, and a wavelength conversion module comprising a plurality of crystals for frequency multiplying and mixing the amplified first and second radiation beams to produce an output beam at a fifth harmonic that is less than about 208 nm.

In a specific implementation, the wavelength conversion module comprises a first 2nd harmonic generator (2HG) for receiving the first radiation beam and generating a 2nd harmonic beam from the first radiation beam, a second 2HG for receiving the second radiation beam and generating a 2nd harmonic beam from the second radiation beam, a $3^{rd}$ harmonic generator (3HG) for receiving the $2^{nd}$ harmonic radiation beam from the second 2HG and mixing with the second radiation beam of fundamental wave, generating a 3rd harmonic beam, a plurality of mirrors for directing the $3^{rd}$ harmonic radiation beam from the second optical path to the first optical path, and a fifth harmonic generator (5HG) for receiving and mixing the $3^{rd}$ harmonic radiation beam and the $2^{nd}$ harmonic radiation beam that was directed by the mirrors to thereby generate the output beam at a 5th harmonic that is less than about 208 nm.

In a further aspect, the first and second 2HG are periodically-poled lithium tantalite (PPLT) crystals; the 3HG is a Lithium Triborate (LBO) crystal; and the 5HG is a Potassium Fluoroboratoberyllate (KBBF) crystal. In this aspect, the $5^{th}$ harmonic is between 180-199 nm. In a specific embodiment, the first laser beam has a wavelength between 800-850 nm and the second laser beam has a wavelength between about 980-1120 nm. In this embodiment, the first amplifier is a Thulium-Doped Fiber Amplifier (TDFA) and the second amplifier is an Ytterbium-Doped Fiber Amplifier (YDFA). In another embodiment, the first laser beam has a wavelength between 905-940 nm and the second laser beam has a wavelength between about 980-1120 nm. In this embodiment, the first amplifier is a Neodymium-Doped Fiber Amplifier (NDFA) and the second amplifier is a YDFA.

In another implementation, the wavelength conversion module comprises a 2nd harmonic generator (2HG) for receiving the second radiation beam and generating a 2nd harmonic beam from the second radiation beam, a $3^{rd}$ harmonic generator (3HG) for receiving the $2^{nd}$ harmonic radiation beam from the 2HG and mixing with the second radiation beam of fundamental wave, generating a 3rd harmonic beam, a plurality of mirrors for directing the 3rd harmonic radiation beam from the second optical path into the first optical, a 4th harmonic generator (4HG) for receiving and mixing the 3rd harmonic radiation beam and the first radiation beam to thereby generate a 4th harmonic beam, and a fifth harmonic generator (5HG) for receiving the 4th harmonic radiation beam and mixing again the 1st radiation beam of fundamental wave to thereby generate the output beam at a 5th harmonic that is less than about 208 nm.

In a further aspect, the 2HG is a PPLT crystal; the 3HG is a LBO crystal; and the 4HG and 5HG are Rubidium fluoroberyllium borate (RBBF) crystals. In this aspect, the $5^{th}$ harmonic is between 180-199 nm. In yet a further aspect, the first laser beam has a wavelength between 800-850 nm and the second laser beam has a wavelength between about 980-1120 nm. In this embodiment, the first amplifier is a TDFA and the second amplifier is a YDFA. In yet another embodiment, the first laser beam has a wavelength between 905-940 nm and the second laser beam has a wavelength between about 980-1120 nm. In this embodiment, the first amplifier is a NDFA and the second amplifier is a YDFA.

In another embodiment, the invention pertains to an inspection system for inspecting a photolithographic reticle or wafer for defects. The system includes any of the above-described a laser apparatus, imaging optics for directing the output beam towards a reticle or wafer, a detector for receiving a detected signal or image in response to the output beam being reflected from or transmitted through the reticle or being reflected from wafer, and a processor and memory that are configured to analyze the detected signal or image to thereby detect defects on the reticle or wafer.

In other embodiments, the invention pertains to a method of generating output radiation having a wavelength below about 208 nm. The method includes generating a first radiation beam having a first fundamental wavelength on a first optical path and a second radiation beam having a second fundamental wavelength on a second optical path; amplifying the first radiation beam; amplifying the second radiation beam; and frequency multiplying and mixing the amplified first and second radiation beams to produce an output beam at a fifth harmonic that is less than about 208 nm. In other embodiments, the operation for multiplying and mixing is performed by any of the above-described components.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

Figure 1:
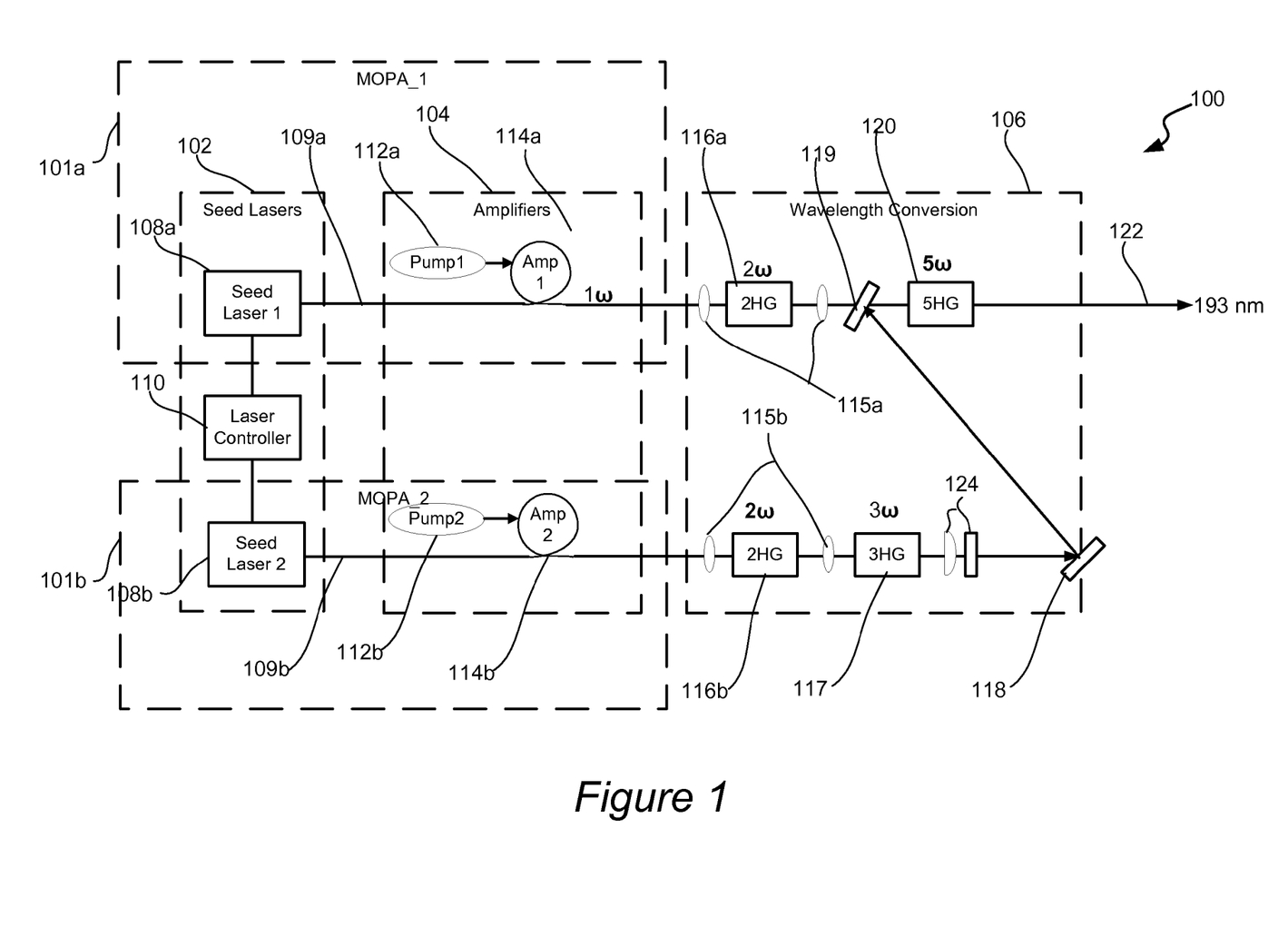
FIG. 1 is a diagrammatic representation of a laser apparatus in accordance with one embodiment of the present invention.

Described herein are embodiments of apparatus and methods for generating Deep Ultra-Violet (DUV) radiation in the sub-200 nm wavelength range for applications in wafer and reticle inspection, as well as any other suitable DUV applications. FIG. 1 is a diagrammatic representation of a laser apparatus 100 in accordance with one embodiment of the present invention. As shown, the laser apparatus may include a pair of master oscillation power amplifiers (MOPA's) 101a and 101b for generating and amplifying two different laser sources. In general, each of the MOPA's 101a and 101b includes a seed laser and amplifier. In a specific implementation, a master oscillation fiber amplifier (MOFA) is utilized. In other cases, a MOPA may take the form of a solid-state bulk laser and a bulk amplifier, or a tunable external-cavity diode laser and a semiconductor optical amplifier.

In the illustrated embodiment, first MOPA 101a comprises a seed radiation source 108a (e.g., from seed module 102) for generating a first radiation beam having a first fundamental wavelength on optical path 109a and a first amplifier 114a for amplifying this first radiation beam. Second MOPA 101b comprises a seed radiation source 108b for generating a second radiation beam having a second fundamental wavelength on optical path 109b and a second amplifier 114b for amplifying this second radiation beam.

Each seed laser source may take any suitable form for generating a laser beam at a particular wavelength that matches the corresponding amplifier. By way of examples, a seed laser source may take the form of a laser diode, short-cavity fiber laser, solid-state laser, distributed feedback (DFB) laser, etc. Although two separate seed lasers are shown in the illustrated examples, a single seed laser may be split to obtain multiple seed lasers.

Although an individual laser at a particular power can be used, use of a MOPA, instead of an individual laser, allows both high power and high beam quality output. That is, a particular performance, e.g., line width, wavelength tuning range, beam quality, and/or pulse duration, can more easily be achieved if such performance requirements are decoupled from the generation of a high power level. This decoupling feature can be especially advantageous if a gain-switch laser diode is used as a seed laser.

A low power seed laser may be utilized to achieve optimum beam quality. The beam quality of a laser generally relates to how tightly the beam can be focused under various conditions while minimizing beam divergence. For example, beam quality can be quantified by a beam product parameter (BPP), which is the product of the beam radius and far-field beam divergence angle, a $M^2$ factor, which is the BPP divided by the corresponding product of a diffraction-limited Gaussian beam with the same wavelength, or the inverse of $M^2$ (which is ideally 1). An optimum beam quality can often be achieved by solid-state bulk lasers operating on a single transverse mode and by fiber lasers based on single-mode fibers, and also by some low-power laser diodes (particularly vertical cavity surface-emitting lasers or VCSELs). However, high power lasers can have a low beam quality. Accordingly, low power seed lasers are preferably used in a MOPA system.

Each seed laser source is controlled by one or more laser controllers, e.g., controller 110. A controller (not shown) can also be used to control the amplifiers and laser pumps. In general, a laser controller can be used to control a seed laser source's (and laser pump's) power, phase, and polarization, as well as operating to cause synchronizing of the output of the first and second radiation beams, via electrical signals. In general, the laser controller is configured to cause generation of two laser radiation pulses with substantially the same pulse repetition rates and respectively fixed phase relations, as well as provide frequencies that are tuned to the range of the respective amplifiers. For example, the controller may include one or more electro-optical modulators (EOM's), pulsed current sources for driving each laser, etc.

Each seed laser source can be fiber coupled to an optical fiber amplifier. Alternatively, any suitable waveguide may be used to cause each seed laser to be incident on its respective amplifier. As shown, the output of the first seed laser source 108a is fiber coupled to first fiber optical amplifier 114a, and the output of the second seed laser source 108b is fiber coupled to second fiber optical amplifier 114b.

The intensity of the output of each optical fiber amplifier depends on the intensity of an excitation light provided by one or more pump lasers. In the illustrated example, a first pump laser 112a provides excitation light to first optical fiber amplifier 114a, and a second pump laser 112b provides excitation light to second optical fiber amplifier 114b. Each optical fiber amplifier may comprise two or multiple stages of amplifications, such as pre-amplifier and main (or booster) amplifier, each with their own suitable pump lasers.

In each optical path of MOFA, the excitation light from a laser pump can produce a population inversion in the corresponding optical amplifier, resulting in an amplified output of the seed laser radiation at a fundamental frequency. The gain medium can be a glass fiber doped with rare earth ions, such as Erbium in an EDFA (Erbium-Doped Fiber Amplifier), Neodymium in an NDFA (Neodymium-Doped Fiber Amplifier), Ytterbium in a YDFA (Ytterbium-Doped Fiber Amplifier), Praseodymium in a PDFA (Praseodymium-Doped Fiber Amplifier), or Thulium in a TDFA (Thulium-Doped Fiber Amplifier).

This active dopant in each amplifier may be pumped with excitation light from a pump laser, such as a fiber coupled laser diode, together with the input beam that is to be amplified. In a particular implementation, the pump lasers could be a Raman fiber laser, which is based on a fiber laser and a cascade Raman resonator with nested pairs of FBGs (fiber Bragg-gratings), where oscillation on one Raman order is used for pumping another order, such to bridge larger frequency offsets.

The laser apparatus 100 also includes a wavelength conversion module 106 that includes a plurality of crystals for frequency multiplying and mixing the amplified first and second radiation sources so as to produce an output radiation 122 at a fifth harmonic that is less than about 200 nm. The wavelength conversion module 106 generally includes a plurality of frequency multipliers and at least one mixer for manipulating the two amplified radiation beams with respect to their fundamental frequencies.

As shown, a $2^{nd}$ harmonic generator (2HG) 116a or frequency doubler receives the first amplified radiation beam with a first fundamental wavelength ($1\omega$) on the first optical path 109a and generates a frequency doubled beam at a $2^{nd}$ harmonic ($2\omega$). In the second optical path 109b, another 2HG 116b receives the second amplified radiation beam and also generates a beam at a $2^{nd}$ harmonic ($2\omega$) of the fundamental incident beam ($1\omega$), and a third harmonic generator (3HG) is then produced by mixing this $2^{nd}$ ($2\omega$) harmonic beam with the original fundamental harmonic ($1\omega$), so as to generate a third harmonic ($3\omega$) beam.

One or more mirrors (e.g., 118 and 119) can then be configured to reflect the resulting third harmonic ($3\omega$) beam onto the first optical path 109a. The mirror (e.g., 119) that is placed within the first optical path 109a is also configured to pass the second harmonic ($2\omega$) beam of the first optical path 109a, as well as reflecting the third harmonic beam ($3\omega$) from the second optical path 109b. For example, mirror 119 is a dichroic mirror.

The laser apparatus 100 may also include a $5^{th}$ harmonic generator (5HG 120) that sum-frequency mixes the 3rd harmonic ($3\omega$) beam with the second harmonic ($2\omega$) beam so as to produce an output beam 122 at the fifth harmonic ($5\omega$) with respect to one of the initial laser fundamental wavelengths ($1\omega$). This $5^{th}$ harmonic ($5\omega$) output beam 122 has a wavelength equal to or less than about 193 nm or sub-200 nm.

One or more additional optical elements may be used within optical paths 109a and 109b. For example, lens 115a and 115b can be used to focus its incoming beams to a desirable shape and size to optimize conversion efficiency of harmonic generation in the associated crystals. Additionally, a pair of cylindrical lens 124 may be used to shape the 3rd harmonic beam in each of the directions individually so as to achieve high conversion efficiency of $5^{th}$ harmonic generation in 5GH.

Figure 2:
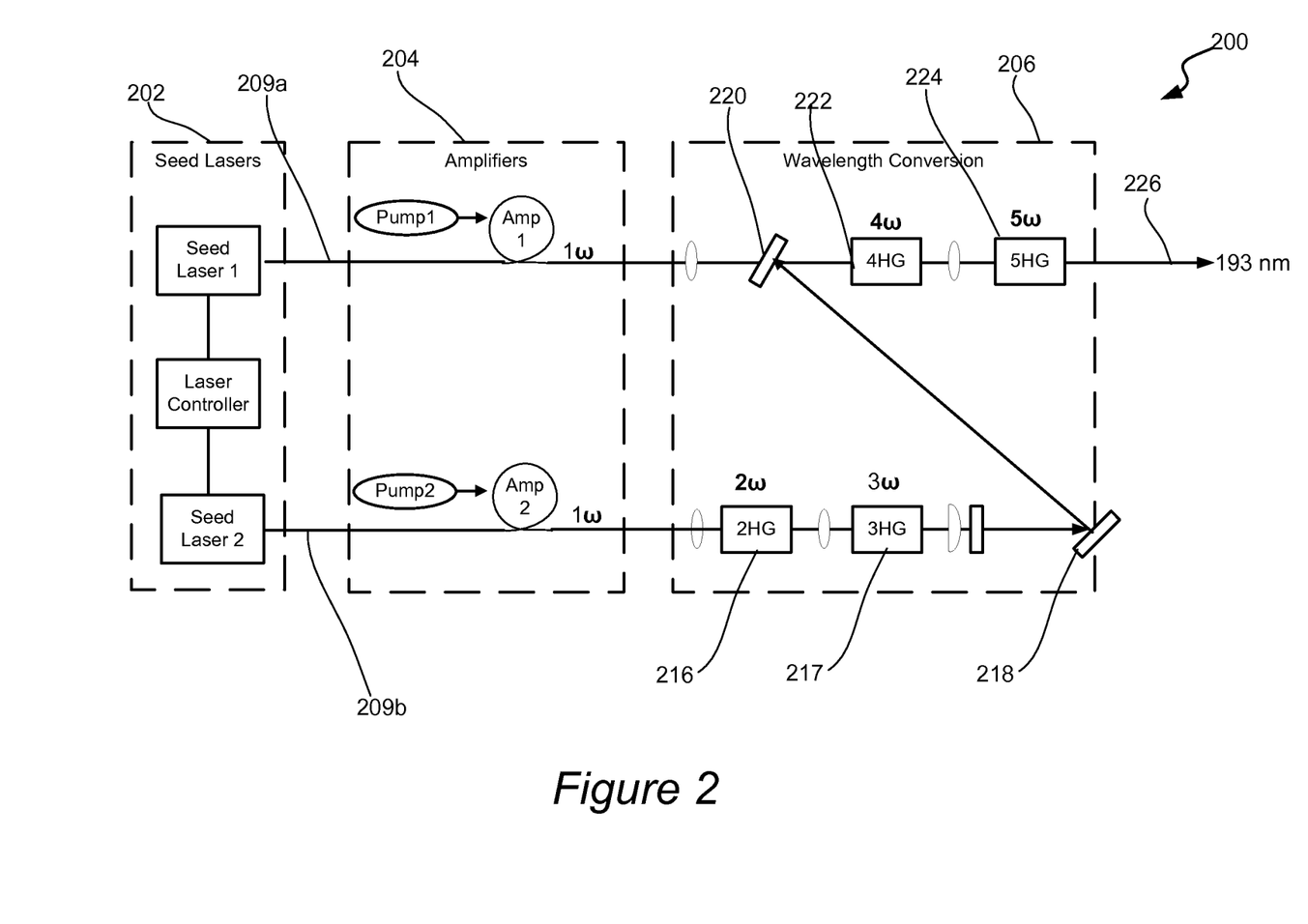
FIG. 2 is a diagrammatic representation of a laser apparatus in accordance with an alternative embodiment of the present invention.

FIG. 2 is a diagrammatic representation of a laser apparatus 200 in accordance with an alternative embodiment of the present invention. As shown, a seed laser module 202 generates two pulsed radiation lasers at fundamental wavelengths/frequencies ($1\omega$) on a first optical path 209a and a second optical path 209b, respectively. An amplifiers module 204 then amplifies such $1\omega$ lasers.

A $2^{nd}$ harmonic generator (2HG) 216 (of wavelength conversion module 206) receives the amplified fundamental beam ($1\omega$) from path 209b and generates a $2^{nd}$ harmonic beam ($2\omega$) that is then mixed with the fundamental beam ($1\omega$) in 3HG 217 to generate a $3^{rd}$ harmonic beam ($3\omega$). This $3^{rd}$ harmonic beam ($3\omega$) is then reflected onto the first optical path 209a, wherein a $4^{th}$ harmonic generator (4HG 222) frequency mixes such $3^{rd}$ harmonic beam ($3\omega$) with the fundamental beam ($1\omega$) from first optical path 209a, so as to generate a $4^{th}$ harmonic beam ($4\omega$). A $5^{th}$ harmonic generator (5HG 224) then receives this $4^{th}$ harmonic ($4\omega$) beam and mixes it again with the fundamental beam ($1\omega$) from path 209a so as to generate a $5^{th}$ harmonic beam 226 at a sub-200 nm wavelength.

Figure 3A:
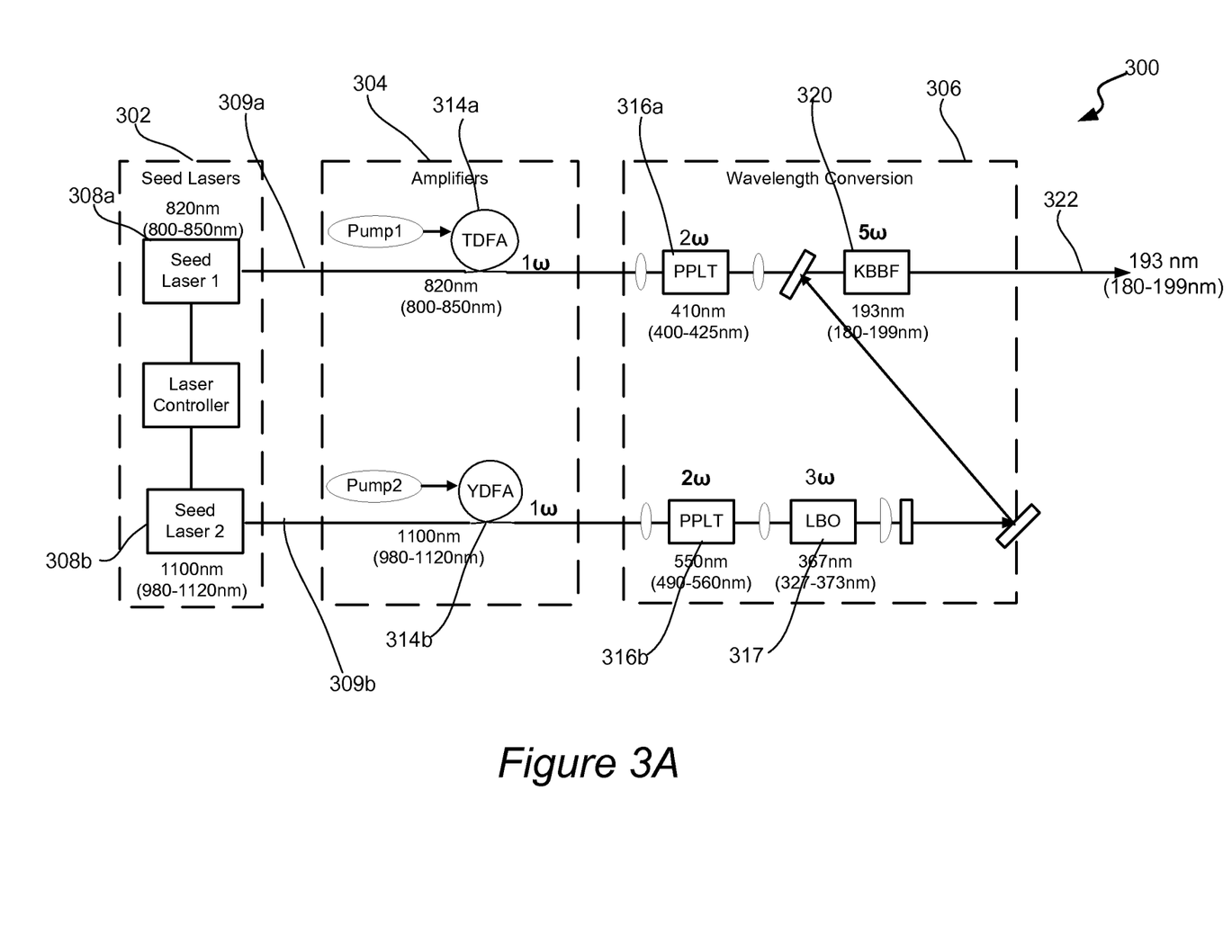
FIG. 3A illustrates a first example implementation of the laser apparatus of FIG. 1.

The first embodiment of FIG. 1 may be implemented using any suitable components. FIG. 3A illustrates a first example implementation of the laser apparatus of FIG. 1. In this example, laser apparatus 300 provides a first seed laser 308a at a wavelength in the range of about 800-850 nm, e.g., 820 nm. The laser apparatus is also arranged to provide a second seed laser source 308b at a wavelength between about 980-1120 nm, e.g., 1100 nm.

The particular fundamental wavelength ranges of the first and second lasers are generally selected to match amplifiers that are formed from particular materials, as well as the amplifier materials being selected to work with the particular desired wavelength ranges. As shown, a Thulium-Doped Fiber Amplifier (TDFA) 314a receives and amplifies the first laser (e.g., 820 nm) and an Ytterbium-Doped Fiber Amplifier (YDFA) 314b receives and amplifies the second laser (e.g., 1100 nm).

In the first optical path 309a, a periodically-poled lithium tantalite or $LiTaO_3$ (PPLT) crystal 316a may be arranged to receive the first amplified ($1\omega$) beam of s-polarized light (e.g., 820 nm) and generate a $2^{nd}$ harmonic ($2\omega$) beam at a wavelength between 400-425 nm (e.g., 410 nm) via a quasi-phase matching condition. Likewise, PPLT 316b receives the second amplified ($1\omega$) beam of p-polarized light (e.g., 1100 nm) and generates a $2^{nd}$ harmonic ($2\omega$) beam of p-polarized at a wavelength between 490-560 nm (e.g., 550 nm), which is passed through a Lithium Triborate (LBO) or $LiB_3O_5$ crystal 317 and mixed with the second amplified (1ω) beam to generate a $3^{rd}$ harmonic (3ω) beam of s-polarized light at a wavelength between about 327-373 nm (e.g., 367 nm) via type I and non-critical phase-matching condition. Instead of a PPLT crystal, PPLN, LBO, PPKTP, PPSLT, or the like, crystals may be used, which may require different phase-matching types and conditions. In the illustrated example, a Potassium Fluoroboratoberyllate, or $KBe_2B0_3F_2$, (KBBF) crystal 320 then receives and sum-frequency mixes the $2^{nd}$ harmonic (2ω) beam from 316a and the $3^{rd}$ harmonic (3ω) beam from 317 to form a $5^{th}$ harmonic (5ω) output beam of p-polarized light having a wavelength range between about 180-199 nm (e.g., 193 nm), via type I critical phase-matching condition. Instead of a KBBF crystal, RBBF, BPO (or BPO4), or the like, crystals may be used, which may require different phase match types and conditions.

Figure 3B:
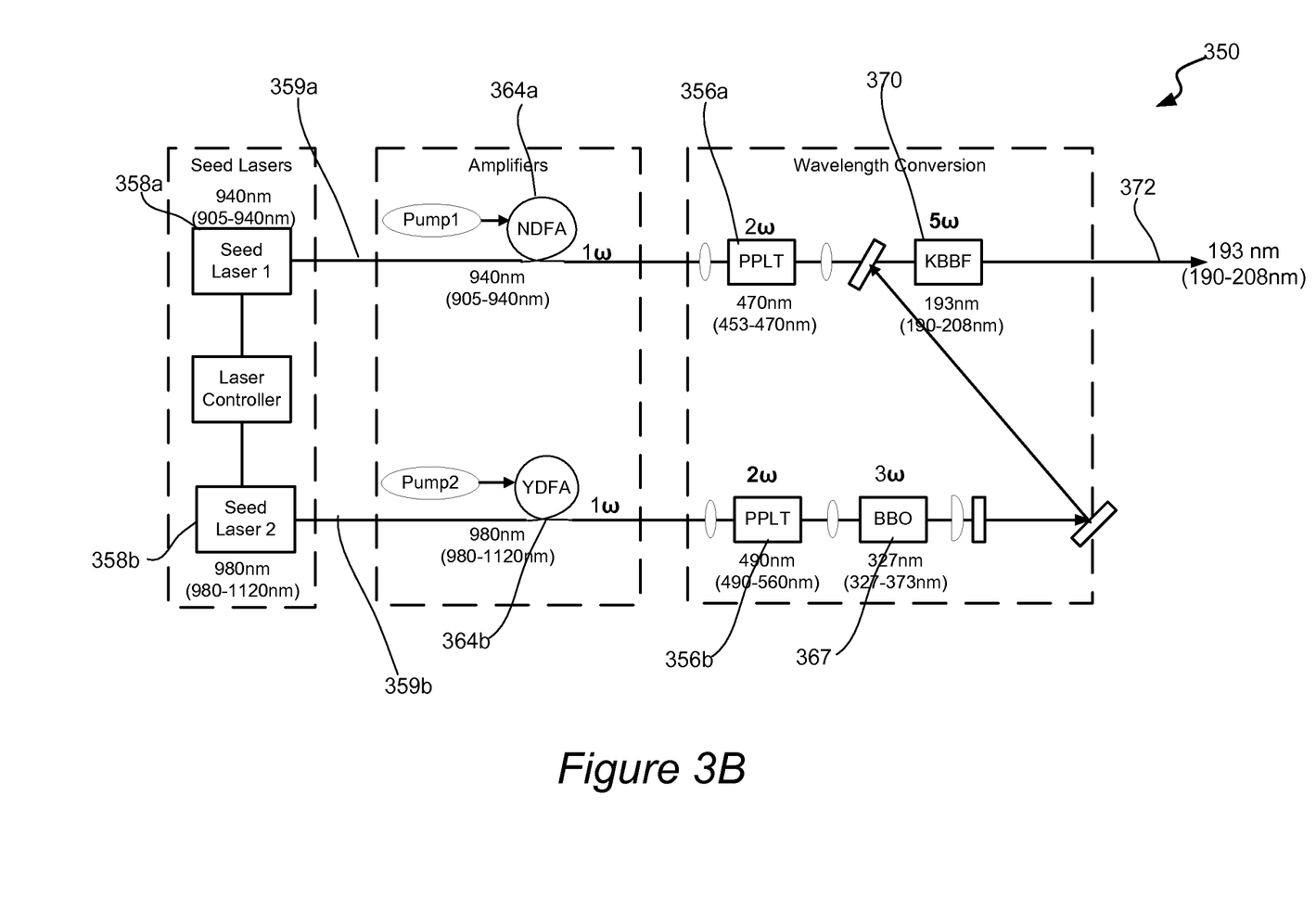
FIG. 3B illustrates a second example implementation of the laser apparatus of FIG. 1.

FIG. 3B illustrates a second example implementation of the laser apparatus of FIG. 1. As shown, laser apparatus 350 includes a seed laser module that provides a first seed laser 358a at a wavelength between about 905-940 nm (e.g., 940 nm) on a first optical path 359a and a second seed laser 358b at a wavelength between about 980-1120 nm (e.g., 980 nm) on a second optical path 359b. The 905-940 nm laser is received by a neodymium (NDFA) amplifier 364a, while the 980-1120 nm laser is received by an YDFA amplifier 364b.

PPLT crystals 356a and 356b generate a 2nd harmonic of these first and second fundamental (1ω) lasers, respectively, of the first and second optical paths 359a and 359b, respectively. That is, PPLT 356a generates a 2nd harmonic beam of s-polarized light at 453-470 nm (e.g., 470 nm), via a quasi-phase matching condition, and similarly PPLT 356b provides a 2nd harmonic at 490-560 nm of p-polarized light (e.g., 490 nm).

On the second optical path 359b, a $3^{rd}$ harmonic generator in the form of a Beta Barium Borate (BBO) crystal 367 receives and mixes the $2^{nd}$ harmonic beam of p-polarized light (e.g., 490 nm) with the fundamental harmonic (1ω) of p-polarized light to obtain a $3^{rd}$ harmonic (3ω) of s-polarized light in the range of 327-373 nm (e.g., 327 nm), via type I critical phase-matching condition This $3^{rd}$ harmonic beam (3ω) is then reflected onto the first optical path into a KBBF crystal 370 and sum frequency mixes with the 2nd harmonic beam of s-polarized light from 356a to generates a $5^{th}$ harmonic output beam of p-polarized light in the range of 190-208 nm (e.g., 193 nm), via type I critical phase-matching condition.

Figure 4A:
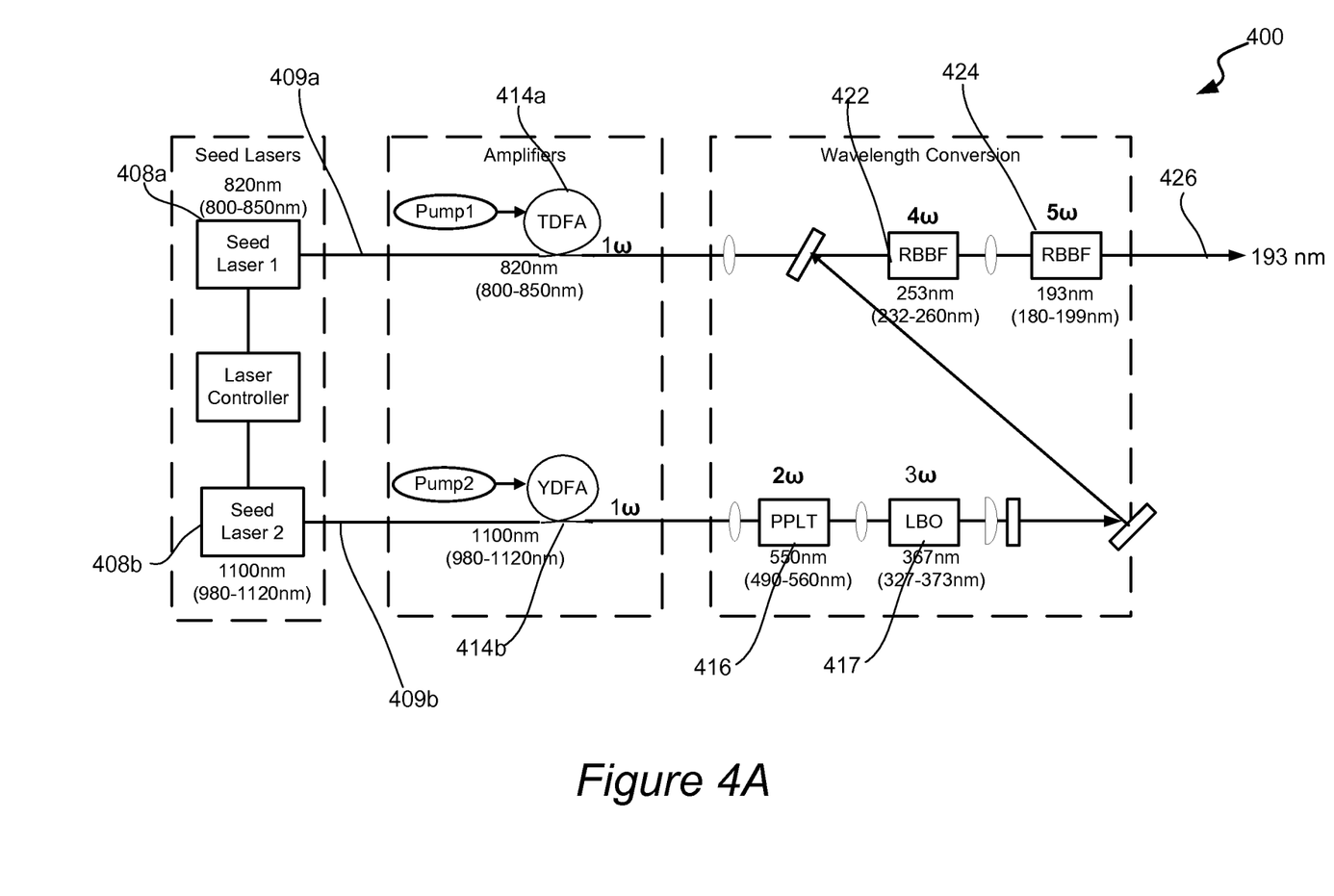
FIG. 4A illustrates a first example implementation of the laser apparatus of FIG. 2.

FIG. 4A illustrates a first example implementation of the alternative laser apparatus of FIG. 2. In this example, a first seed laser 408a at a wavelength between about 800-850 nm (e.g., 820 nm) is generated and input to TDFA amplifier 414a on a first optical path 409a, while a second seed laser 408b at a wavelength between about 980-1120 nm (e.g., 1100 nm) is generated and input to a YDFA amplifier 414b on a second optical path 409b.

On the second optical path 409b, a PPLT crystal 416 generates a $2^{nd}$ harmonic of the second laser at a wavelength between about 490-560 nm of p-polarized light (e.g., 550 nm) via a quasi-phase matching condition, which is then mixed with the original fundamental harmonic of p-polarized light by a LBO crystal 417, via a type I non-critical phase-matching condition to achieve a $3^{rd}$ harmonic of s-polarized light at a wavelength between about 327-373 nm (e.g., 367 nm). This $3^{rd}$ harmonic beam is then reflected onto the first optical path 409a and mixed with the fundamental harmonic beam of p-polarized light of the first path 409a in Rubidium fluoroberyllium borate (RBBF) crystal 422 so as to generate a $4^{th}$ harmonic of p-polarized light, via a type II critical phase-matching condition at a wavelength between about 232-260 nm (e.g., 253 nm), which is then again mixed with the fundamental harmonic of p-polarized light of the first optical path by a RBBF crystal 424 to generate a $5^{th}$ harmonic beam of s-polarized light at a wavelength between 180-199 nm (e.g., 193 nm) via a type I critical phase-matching condition (CPM). A KBBF, BBO, and BPO (or BPO4) may be used in place of a RBBF crystal, which may require a different phase-matching type and condition.

Figure 4B:
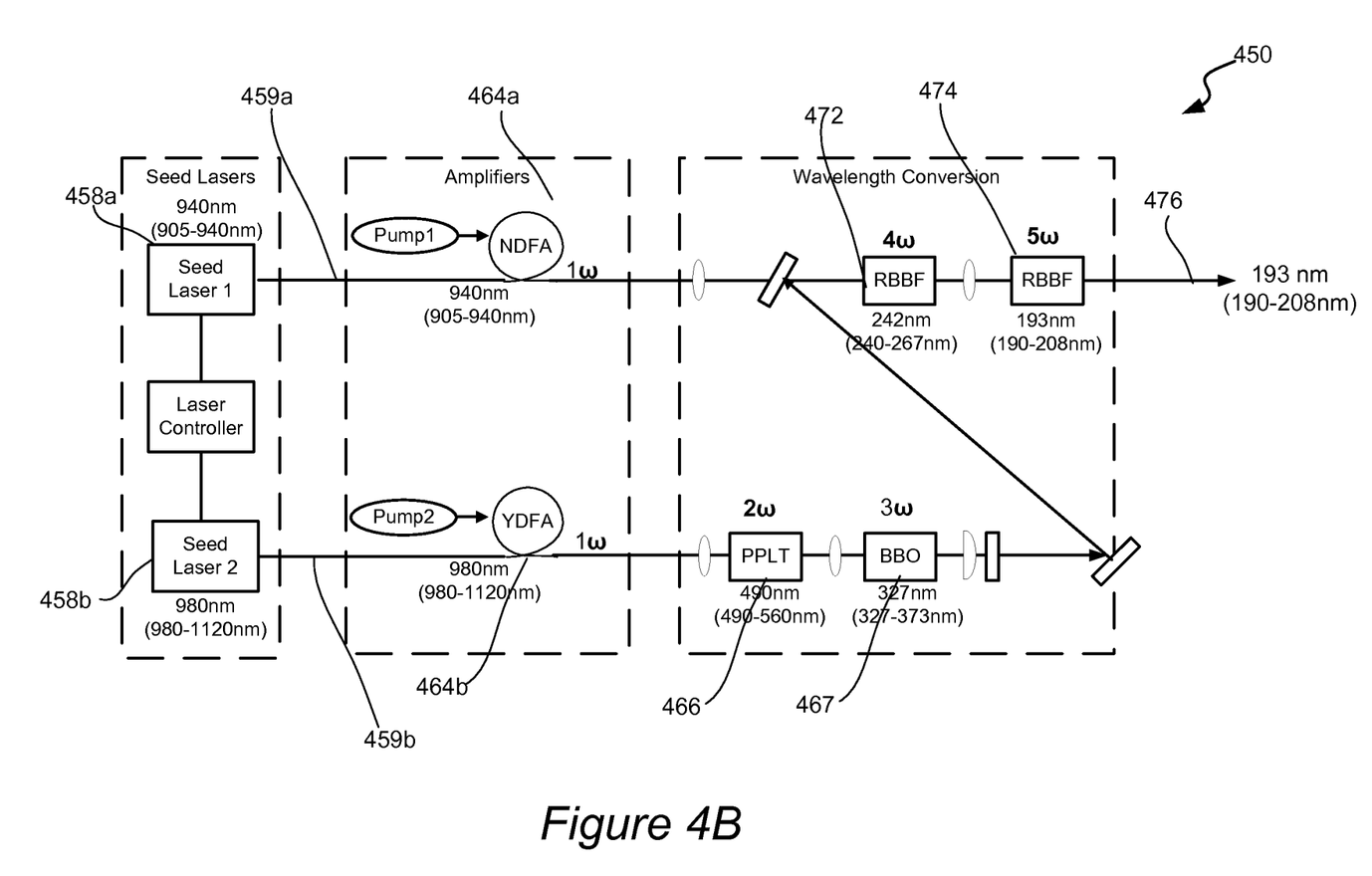
FIG. 4B illustrates a second example implementation of the laser apparatus of FIG. 2.

FIG. 4B illustrates a second example implementation of the laser apparatus of FIG. 2. In this example, a first seed laser 458a is generated at a wavelength between about 905-940 nm (e.g., 940 nm) on a first optical path 459a, while a second seed laser 458b is generated at a wavelength between about 980-1120 nm (e.g., 980 nm) on a second optical path 459a. The first seed laser 458a is amplified by an NDFA amplifier 464a, while the second seed laser 458b is amplified by an YDFA amplifier 464b.

A PPLT crystal 466 receives the second amplified laser on the second optical path 459b and generates a $2^{nd}$ harmonic beam of p-polarized light at a wavelength between about 490-560 nm (e.g., 490 nm), via a quasi-phase matching condition, which is input to a BBO crystal 467 that mixes this $2^{nd}$ harmonic (2ω) with the original fundamental harmonic (1ω) of p-polarized light and generates a $3^{rd}$ harmonic (3ω) of s-polarized light at a wavelength between about 327-373 nm (e.g., 327 nm) via a type I critical phase-matching condition. This $3^{rd}$ harmonic is then reflected onto the first optical path 459a and mixed with the fundamental wave of p-polarized light of first optical path in a RBBF crystal 472 to produces a $4^{th}$ harmonic beam of p-polarized light at a wavelength between about 240-267 nm (e.g., 242 nm), via a type II critical phase-matching condition, which is then mixed with the original fundamental beam p-polarized light of the first optical path 459a in another RBBF crystal 474 to produce a $5^{th}$ harmonic output beam 476 of s-polarized light, having a wavelength between about 190-208 nm (e.g., 193 nm), via a type I critical phase-matching condition.

Certain embodiments offer a simplified and efficient mechanism for building DUV sub-200 nm laser sources. A sub-200 nm laser is obtained via a 5th harmonic (5ω) conversion. Use of frequency-tripling (3ω) and application of KBBF crystals may entail high efficiency, and may be used to achieve higher output power DUV sub-200 nm range laser system.

System Examples:

The laser apparatus described herein may be integrated into any suitable optical system. Example systems may include a photolithography system, semiconductor wafer or reticle inspection or metrology tool, etc.

Figure 5A:
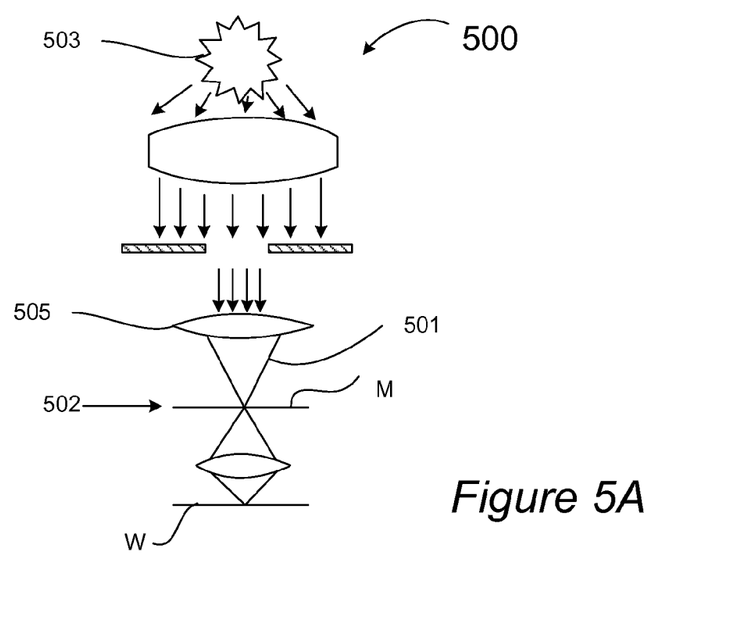
FIG. 5A is a simplified schematic representation of a lithographic system for transferring a mask pattern from a photomask onto a wafer in accordance with certain embodiments.

FIG. 5A is a simplified schematic representation of a typical lithographic system 500 that can be used to transfer a mask pattern from a photomask M onto a wafer W in accordance with certain embodiments. Examples of such systems include scanners and steppers, more specifically PAS 5500 system available from ASML in Veldhoven, Netherlands. In general, an illumination source 503 directs a light beam through an illumination lens 505 onto a photomask M located in a mask plane 502.

The illumination source 503 may take the form of any of the laser apparatus described herein. The illumination lens 505 has a numeric aperture 501 at that plane 502. The value of the numerical aperture 501 impacts which defects on the photomask are lithographic significant defects and which ones are not. A portion of the beam that passes through the photomask M forms a patterned optical signal that is directed through imaging optics 553 and onto a wafer W to initiate the pattern transfer.

Figure 5B:
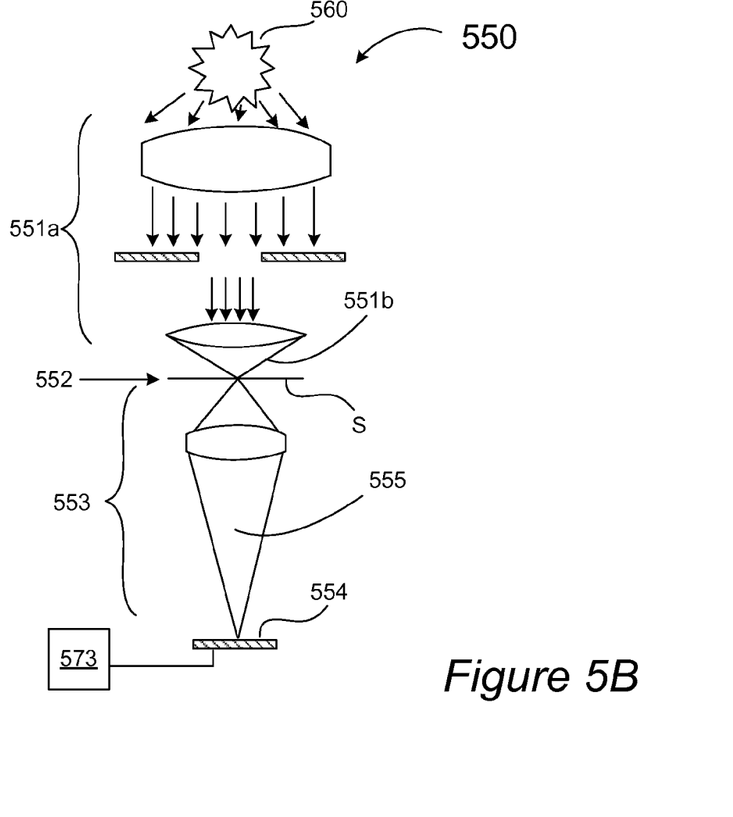
FIG. 5B provides a schematic representation of an inspection apparatus in accordance with certain embodiments.

FIG. 5B provides a schematic representation of an inspection (or metrololgy) system 550 that has an imaging lens 551a with a relative large numerical aperture 551b at a plane 552 in accordance with certain embodiments. The depicted inspection system 550 includes microscopic magnification optics 553 designed to provide, for example, 60-200× magnification for enhanced inspection. The numerical aperture 551b at the plane 552 of the inspection system is often considerable greater than the numerical aperture 501 at the plane 502 of the lithography system 500, which would result in differences between test inspection images and actual printed images. Each of these optical systems (500, 550) induces different optical effects in the produced images, and such systems can implement techniques for compensating for such effects during an inspection or metrology process.

The laser apparatus herein may be implemented on various specially configured inspection systems, such as the one schematically illustrated in FIG. 5B. The system 550 includes an illumination source 560 producing a laser beam that is directed through illumination optics 551 onto a sample S, such as a photomask or wafer in the plane 552. The light source can take the form of any laser apparatus described herein so as to generate light that has a wavelength that is about 193 nm. As explained above, the inspection system 550 has a numerical aperture 551b at the plane 552 that may be greater than a plane numerical aperture (e.g., element 501 in FIG. 5A) of the corresponding lithography system. The sample S to be inspected is placed at the plane 552 and exposed to the source.

The patterned image from the sample S is directed through a collection of magnification optical elements 553, which project the patterned image onto a sensor 554. Suitable sensors include charged coupled devices (CCD), CCD arrays, time delay integration (TDI) sensors, TDI sensor arrays, photomultiplier tubes (PMT), and other sensors. In a reflecting system, optical elements would illuminate the sample and capture the reflected image.

The signals captured by the sensor 554 can be processed by a computer system 573 or, more generally, by a signal processing device, which may include an analog-to-digital converter configured to convert analog signals from the sensor 554 into digital signals for processing. The computer system 573 may be configured to analyze intensity, phase, and/or other characteristics of the sensed light beam. The computer system 573 may be configured (e.g., with programming instructions) to provide a user interface (e.g., on a computer screen) for displaying resultant test images and other inspection characteristics. The computer system 573 may also include one or more input devices (e.g., a keyboard, mouse, joystick) for providing user input, such as changing detection threshold. In certain embodiments, the computer system 573 is configured to carry out inspection techniques detailed below. The computer system 573 typically has one or more processors coupled to input/output ports, and one or more memories via appropriate buses or other communication mechanisms.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, a system for inspecting a sample includes at least one memory and at least one processor that are configured to perform the following operations: producing test light intensity images of a sample that include a test transmitted image and/or a test reflected image and analyzing the test light intensity images based on a reference image (from an imaged sample or from a design database) to identify defects.

It should be noted that the above diagrams and description are not to be construed as a limitation on the specific components of the system and that the system may be embodied in many other forms. For example, it is contemplated that the inspection or measurement tool may be any of a number of suitable and known imaging or metrology tools arranged for resolving the critical aspects of features of a reticle or wafer. By way of example, an inspection or measurement tool may be adapted for bright field imaging microscopy, darkfield imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may be contemplated.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A laser apparatus for generating output radiation having a wavelength below about 208 nm, comprising:
    one or more seed radiation sources for generating a first radiation beam having a first fundamental wavelength on a first optical path and a second radiation beam having a second fundamental wavelength on a second optical path, wherein the first radiation beam has a wavelength between 800-850 nm or 905-940 nm and the second radiation beam has a wavelength between about 980-1120 nm;
    a first amplifier for amplifying the first radiation beam;
    a second amplifier for amplifying the second radiation beam; and
    a wavelength conversion module for frequency multiplying and mixing the amplified first and second radiation beams to produce an output beam at a fifth harmonic that is less than about 208 nm, wherein the wavelength conversion module comprises:
        a 2nd harmonic generator (2HG) for receiving the second radiation beam and generating a 2nd harmonic beam by doubling a frequency of the second radiation beam;

a 3$^{rd}$ harmonic generator (3HG) for receiving and mixing the 2$^{nd}$ harmonic radiation beam with the second radiation beam to generate a 3rd harmonic beam;

a 4$^{th}$ harmonic generator (4HG) for receiving and mixing the first radiation beam with the 3$^{rd}$ harmonic beam to generate a 4$^{th}$ harmonic beam; and a fifth harmonic generator (5HG) for generating the output beam at a 5th harmonic that is less than about 208 nm by receiving and mixing the 4th harmonic radiation beam and the first radiation beam.

2. The laser apparatus of claim 1, wherein the wavelength conversion module further comprises:

a plurality of mirrors for directing the 3rd harmonic radiation beam to merge with the first radiation beam of the first optical path.

3. The laser apparatus of claim 2, wherein the first radiation beam has a wavelength between 800-850 nm, wherein the first amplifier is a TDFA and the second amplifier is a YDFA, wherein the 2HG is a PPLT crystal, the 3HG is a LBO crystal, the 4HG and 5HG are Rubidium fluoroberyllium borate (RBBF) crystals, wherein the 5$^{th}$ harmonic is between 180-199 nm.

4. The laser apparatus of claim 2, wherein the first radiation beam has a wavelength between 905-940 nm, wherein the first amplifier is a NDFA and the second amplifier is a YDFA, wherein the 2HG is a PPLT crystal, the 3HG is a BBO crystal, the 4HG and 5HG are RBBF crystals, wherein the 5$^{th}$ harmonic reaches between 190-208 nm.

5. An inspection system for inspecting a photolithographic reticle or wafer for defects, comprising:

a laser apparatus as recited in any of claim 1 or 2 4;

imaging optics for directing the output beam towards a reticle or wafer;

a detector for receiving a detected signal or image in response to the output beam being reflected from or transmitted through the reticle or in response to the output beam being reflected from the wafer; and a processor and memory that are configured to analyze the detected signal or image to thereby detect defects on the reticle or wafer.

6. A photolithography system for transferring a pattern from a reticle onto a wafer, comprising:

a laser apparatus as recited in claim 1; and imaging optics for directing the output beam through a reticle onto a wafer.

7. A method of generating output radiation having a wavelength below about 208 nm, comprising:

generating a first radiation beam having a first fundamental wavelength on a first optical path and a second radiation beam having a second fundamental wavelength on a second optical path, wherein the first radiation beam has a wavelength between 800-850 nm or 905-940 nm and the second radiation beam has a wavelength between about 980-1120 nm;

amplifying the first radiation beam;

amplifying the second radiation beam; and frequency multiplying and mixing the amplified first and second radiation beams to produce an output beam at a fifth harmonic that is less than about 208 nm, wherein the operation of multiplying and mixing is performed by:

a 2nd harmonic generator (2HG) for receiving the second radiation beam and generating a 2nd harmonic beam by doubling a frequency of the second radiation beam;

a 3$^{rd}$ harmonic generator (3HG) for receiving and mixing the 2$^{nd}$ harmonic radiation beam with the second radiation beam to generate a 3rd harmonic beam;

a 4$^{th}$ harmonic generator (4HG) for receiving and mixing the first radiation beam with the 3$^{rd}$ harmonic beam to generate a 4$^{th}$ harmonic beam; and a fifth harmonic generator (5HG) for generating the output beam at a 5th harmonic that is less than about 208 nm by receiving and mixing the 4th harmonic radiation beam and the first radiation beam.

8. The method of claim 7, wherein the operation for multiplying and mixing is performed by:

a plurality of mirrors for directing the 3rd harmonic radiation beam to merge with the first radiation beam.

9. The method of claim 8, wherein the first radiation beam has a wavelength between 800-850 nm, wherein the first amplifier is a TDFA and the second amplifier is a YDFA, wherein the 2HG is a PPLT crystal, the 3HG is a LBO crystal, the 4HG and 5HG are RBBF crystals, wherein the 5$^{th}$ harmonic is between 180-199 nm.

10. The method of claim 8, wherein the first radiation beam has a wavelength between 905-940 nm, wherein the first amplifier is a NDFA and the second amplifier is a YDFA, wherein the 2HG is a PPLT crystal, the 3HG is a BBO crystal, the 4HG and 5HG are RBBF crystals, wherein the 5$^{th}$ harmonic is between 190-208 nm.

* * * * *